(12) United States Patent
Sunkara et al.

(10) Patent No.: US 7,038,092 B2
(45) Date of Patent: May 2, 2006

(54) PURIFICATION OF CHEMICAL 1,3-PROPANEDIOL

(75) Inventors: Hari Babu Sunkara, Hockessin, DE (US); Mayis Seapan, Landenberg, PA (US); George F. Diffendall, Wilmington, DE (US); Tyler T. Ames, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/203,029

(22) Filed: Aug. 12, 2005

(65) Prior Publication Data

US 2005/0272962 A1 Dec. 8, 2005

Related U.S. Application Data

(63) Continuation of application No. 10/634,666, filed on Aug. 5, 2003.

(60) Provisional application No. 60/468,223, filed on May 6, 2003.

(51) Int. Cl.
*C07C 43/11* (2006.01)
*C07C 43/13* (2006.01)
*C07C 29/74* (2006.01)
*C07C 29/88* (2006.01)
*C07C 27/90* (2006.01)

(52) U.S. Cl. .................. 568/619; 568/868; 568/869; 568/852; 568/854

(58) Field of Classification Search ............... 568/868, 568/869, 852, 854, 619
See application file for complete search history.

(56) References Cited

U.S. PATENT DOCUMENTS

| | | |
|---|---|---|
| 2,520,733 A | 8/1950 | Morris et al. |
| 3,326,985 A | 6/1967 | Mason et al. |
| 4,213,000 A | 7/1980 | Coates |
| 4,885,410 A | 12/1989 | De Thomas |
| 5,015,789 A | 5/1991 | Arntz et al. |
| 5,171,898 A | 12/1992 | Arntz et al. |
| 5,276,201 A | 1/1994 | Haas et al. |
| 5,284,979 A | 2/1994 | Haas et al. |
| 5,334,778 A | 8/1994 | Haas et al. |
| 5,364,984 A | 11/1994 | Arntz et al. |
| 5,364,987 A | 11/1994 | Haas et al. |
| 5,527,973 A | 6/1996 | Kelsey |
| 5,633,362 A | 5/1997 | Nagarajan et al. |
| 5,686,276 A | 11/1997 | Laffend et al. |
| 5,786,524 A | 7/1998 | Powell et al. |
| 5,821,092 A | 10/1998 | Nagarajan et al. |
| 5,962,745 A | 10/1999 | Brossmer et al. |
| 5,981,808 A | 11/1999 | Powell et al. |
| 5,986,145 A | 11/1999 | Powell et al. |
| 6,111,137 A | 8/2000 | Suizu et al. |
| 6,140,543 A | 10/2000 | Brossmer et al. |
| 6,191,321 B1 | 2/2001 | Forschner et al. |
| 6,232,511 B1 | 5/2001 | Haas et al. |
| 6,235,948 B1 | 5/2001 | Sunkara et al. |
| 6,245,844 B1 | 6/2001 | Kurian et al. |
| 6,255,442 B1 | 7/2001 | Kurian et al. |
| 6,281,325 B1 | 8/2001 | Kurian et al. |
| 6,284,930 B1 | 9/2001 | Haas et al. |
| 6,297,408 B1 | 10/2001 | Haas et al. |
| 6,325,945 B1 | 12/2001 | Kurian et al. |
| 6,331,264 B1 | 12/2001 | Kurian et al. |
| 6,335,421 B1 | 1/2002 | Kurian et al. |
| 6,342,464 B1 | 1/2002 | Arhancet et al. |
| 6,342,646 B1 | 1/2002 | Haas et al. |

(Continued)

FOREIGN PATENT DOCUMENTS

| | | |
|---|---|---|
| DE | 3927645 | 6/1988 |
| EP | 657529 | 12/1993 |
| WO | WO 2004/076392 A1 | 9/2004 |

OTHER PUBLICATIONS

S.V. Conjeevaram, R.S. Benson, and D.J. Lyman, Department of Materials Science and Engineering, University of Utah, Salt Lake City, Utah 84112, Journal of Polymer Science: Polymer Chemistry Edition, vol. 23, 429-444 (1985).

(Continued)

*Primary Examiner*—Elvis O. Price
(74) *Attorney, Agent, or Firm*—Mark D. Kuller; Bart E. Lerman

(57) ABSTRACT

Disclosed is a process comprising contacting chemical 1,3-propanediol with hydrogen in the presence of a hydrogenation catalyst. Preferably, the chemical 1,3-propanediol, before the contacting has an initial color and, after the contacting, has a color that is lower than the initial color.

23 Claims, No Drawings

U.S. PATENT DOCUMENTS

| | | |
|---|---|---|
| 6,350,895 B1 | 2/2002 | Kurian |
| 6,353,062 B1 | 3/2002 | Giardino et al. |
| 2002/0007043 A1 | 1/2002 | Sunkara et al. |
| 2002/0010374 A1 | 1/2002 | Sunkara et al. |
| 2004/0087819 A1 | 5/2004 | Powell et al. |
| 2004/0211729 A1 | 10/2004 | Sunkara et al. |
| 2004/0225107 A1 | 11/2004 | Sunkara et al. |
| 2004/0225162 A1 | 11/2004 | Sunkara et al. |
| 2004/0225163 A1 | 11/2004 | Sunkara et al. |
| 2005/0020805 A1 | 1/2005 | Sunkara et al. |

OTHER PUBLICATIONS

S.M. Ghoreishi and M.R. Haghighi, Characterization and Reduction of Chromophores in Pulp Mill Effluents, Scientic Iranica, vol. 4, No. 3, pp. 131-138, Sharif University of Technology, Oct. 1997.

Herbert O. House, Modern Synthetic Reactions (second edition), W.A. Benjamin, Inc., Menlo Park, California,Reading, Massachusetts, London, Amsterdam, Don Mills, Ontario, Sydney, 1972.

Shigeo Nishimura, Professor Emeritus, Tokyo University of Agriculture and Technology, Handbrook of Heterogeneous Catalytic Hydrogenation for Organic Synthesis, A Wiley-Interscience Publication, John Wiley & Sons, Inc., New York, Chicheste, Weinheim, Brisbane, Singapore, Toront.

International Search Repon; Date Mailed-Jun. 3, 2005.

Written Opinion: Date Mailed-Jun. 3, 2005.

PURIFICATION OF CHEMICAL 1,3-PROPANEDIOL

PRIORITY

This application is a continuation of U.S. application Ser. No. 10/634,666, filed 5 Aug. 2003, and currently pending, which claims priority from Provisional U.S. Patent Application Ser. No. 60/468,223, filed May 6, 2003 and now abandoned, both of which are incorporated herein by reference.

FIELD OF THE INVENTION

This invention relates to removal of color and color precursors from chemically derived 1,3-propanediol by hydrogenation.

BACKGROUND OF THE INVENTION 1,3-Propanediol (also hereinafter termed "PDO") is a monomer useful in the production of a variety of polymers including polyesters, polyurethanes, polyethers, and cyclic compounds. Homo and copolyethers of polytrimethylene ether glycol (hereinafter termed "PO3G") are examples of such polymers. The polymers are ultimately used in various applications including fibers, films, etc.

Chemical routes to generate 1,3-propanediol are known. For instance, 1,3-propanediol may be prepared from:
1. ethylene oxide over a catalyst in the presence of phosphine, water, carbon monoxide, hydrogen and an acid (the "hydroformylation route");
2. the catalytic solution phase hydration of acrolein followed by reduction (the "acrolein route").

Both of these synthetic routes to 1,3-propanediol involve the intermediate synthesis of 3-hydroxypropionaldehyde (hereinafter also termed "HPA"). The HPA is reduced to PDO in a final catalytic hydrogenation step. Subsequent final purification involves several processes, including vacuum distillation. Hereinafter, the PDO from chemical processes is termed "chemical 1,3-propanediol" or "chemical PDO". Chemical PDO is from non-renewable resources, typically petrochemical products. By contrast, biochemically or fermentatively produced 1,3-propanediol or PDO is, by definition, from renewable resources.

Biochemical routes to 1,3-propanediol have been described that utilize feedstocks produced from biological and renewable resources such as corn feed stock. Such PDO is hereinafter referred to as "biochemical PDO" or "biochemically-derived PDO". For example, bacterial strains able to convert glycerol into 1,3-propanediol are found in e.g., in the species *Klebsielia, Citrobacter, Clostridium*, and *Lactobacillus*. The technique is disclosed in several patents, including, U.S. Pat. Nos. 5,633,362, 5,686,276, and, most recently, U.S. Pat. No. 5,821,092, all of which are incorporated herein by reference. In U.S. Pat. No. 5,821,092, Nagarajan et al., disclose inter alia, a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Since both bacteria and yeasts can convert glucose (e.g., corn sugar) or other carbohydrates to glycerol, the process of the invention provided a rapid, inexpensive and environmentally responsible source of 1,3-propanediol monomer useful in the production of polyesters, polyethers, and other polymers.

Precipitations (e.g., with 1,2-propylene glycol, as well as carboxylates or other materials) have been used since the early 1980's to separate the colored and odiferous components from desired products (such as enzymes) to obtain purified preparations. Precipitating the high molecular weight constituents from the fermentor liquors, then bleaching these components with a reducing agent (DE3917645) is known. Alternately, microfiltration followed by nanofiltration to remove the residual compounds has also been found helpful (EP657529) where substances with a high molecular weight above the size of separation are held back. However, nanofiltration membranes become clogged quickly and can be quite expensive.

Various treatment methods are disclosed in the prior art to remove color precursors present in the PDO, however, the methods are laborious, expensive and increase the cost of the polymer. For instance, Kelsey, U.S. Pat. No. 5,527,973, discloses a process for providing a purified 1,3-propanediol that can be used as a starting material for low color polyester. That process has several disadvantages including the use of large equipment and the need for dilution with large quantities of water, which are difficult to remove from the product. Sunkara et al., U.S. Pat. No. 6,235,948, discloses a process for the removal of color-forming impurities from 1,3-propanediol by a preheating, preferably with heterogeneous acid catalysts such as perfluorinated ion exchange polymers. The catalyst is filtered off, and the 1,3-propanediol is then isolated, preferably by vacuum distillation. Preparation of polytrimethylene ether glycol from purified diol gave APHA values of 30–40, however, the molecular weight of the polymers were not reported.

The polyalkylene ether glycols are generally prepared by the acid-catalyzed elimination of water from the corresponding alkylene glycol or the acid-catalyzed ring opening of the alkylene oxide. For example, polytrimethylene ether glycol can be prepared by dehydration of 1,3-propanediol or by ring opening polymerization of oxetane using soluble acid catalysts. Methods for making PO3G from the glycol, using sulfuric acid catalyst, are fully described in U.S. Patent Application publication Nos. 2002/0007043A1 and 2002/0010374A1, all of which are incorporated herein by reference. The polyether glycol prepared by the process is purified by the methods known in the art. The purification process for polytrimethylene ether glycol typically comprises (1) a hydrolysis step to hydrolyze the acid esters formed during the polymerization (2) water extraction steps to remove the acid catalyst, unreacted monomer, low molecular weight linear oligomers and oligomers of cyclic ethers, (3) a base treatment, typically with a slurry of calcium hydroxide, to neutralize and precipitate the residual acid present, and (4) drying and filtration of the polymer to remove the residual water and solids.

It is well known that the polytrimethylene ether glycol produced from the acid catalyzed polycondensation of 1,3-propanediol has quality problems, in particular, the color is not acceptable to the industry. The polymer quality is in general dependent on the quality of the raw material, PDO. Besides the raw material, the polymerization process conditions and stability of the polymer are also responsible for discoloration to some extent. Particularly in the case of polytrimethylene ether glycol, the polyether diols tend to have light color, a property that is undesirable in many end-uses. The polytrimethylene ether glycols are easily discolored by contact with oxygen or air, particularly at elevated temperatures, so the polymerization is effected under a nitrogen atmosphere and the polyether diols are stored in the presence of inert gas. As an additional precaution, a small concentration of a suitable antioxidant is added. Preferred is butylated hydroxytoluene (BHT, 2.6-di-t-butyl-4-methylphenol) at a concentration of about 100–500 microg/g (micrograms/gram) polyether.

Also, attempts have been made to reduce the color of polytrimethylene ether glycols by conventional means without much success. For instance, Morris et al., U.S. Pat. No. 2,520,733, notes the peculiar discoloration tendency for the polytrimethylene ether glycol from the polymerization of PDO in the presence of acid catalyst. The many methods they tried that failed to improve the color of polytrimethylene glycols included the use of activated carbons, activated aluminas, silica gels, percolation alone, and hydrogenation alone. Consequently, they developed a process for the purification of polyols prepared from 1,3-propanediol in the presence of acid catalyst (2.5 to 6% by weight) and at a temperature from about 175° C. to 200° C. This purification process involves percolation of the polymer through Fuller's earth followed by hydrogenation. This extensive purification process gave a final product that was light yellow in color, in fact, this procedure yielded polytrimethylene ether glycol (Example XI therein) for which the color was only reduced to an 8 Gardner color, a quality corresponding to an APHA value of >300 and totally inadequate for current requirements hydrogenation.

Mason in U.S. Pat. No. 3,326,985 discloses a procedure for the preparation of polytrimethylene ether glycol of molecular weights in the range of 1200–1400 possessing improved color by vacuum stripping, under nitrogen, polytrimethylene ether glycol of lower molecular weight. The color levels, however, are not quantified and would not have approached the above requirement.

Catalytic hydrogenation is the reaction of a compound with hydrogen in the presence of a catalyst. Hydrogenation has been used to remove color-causing compounds in the production of certain products from wastewater streams of the kraft pulp mill process (Ghoreishi et al., Characterization and Reduction of Chromophores in Pulp Mill Effluents. *Sci. Iran.* 4(3):131–138 (1997)). A variety of substances are poisons for hydrogenation catalysts; the most commonly encountered being mercury, divalent sulfur compounds, and, to a lesser degree, amines (H. O House, *Modern Synthetic Reactions*, Second ed., W. A. Benjamin: Menlo Park, Calif., pp 1–15 (1972)).

SUMMARY OF THE INVENTION

Disclosed is a process comprising contacting chemical 1,3-propanediol with hydrogen in the presence of a hydrogenation catalyst. Preferably, the chemical 1,3-propanediol, before the contacting has an initial color and, after the contacting, has a color that is lower than the initial color.

DETAILED DESCRIPTION OF THE INVENTION

Unless stated otherwise, all percentages, parts, ratios, etc., are by weight. Trademarks are shown in upper case.

Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed.

The present invention is directed towards a hydrogenation process for chemical PDO. In accordance with a first aspect, a process comprises contacting chemical 1,3-propanediol with hydrogen in the presence of a hydrogenation catalyst. Preferably, the chemical 1,3-propanediol, before the contacting has an initial color and, after the contacting, has a color that is lower than the initial color.

By the terms "remove" or "removal", as applied to color and color precursors, is meant a chemical conversion by hydrogenation. Chemicals that cause color, or have the potential to cause color in subsequent processing, are "removed", i.e., converted into chemicals that are not colored and do not have the potential to cause color in subsequent processing.

By the term "color" is meant the existence of visible color that can be quantified using a spectrocolorimeter in the range of visible light, using wavelengths of approximately 400–800 nm, and by comparison with pure water. Color precursors in chemical PDO are not visible in this range, but subsequently react to give compounds that contribute color in the polyester, polyether glycol, and polyester diols during polymerization or isolation. While not wishing to be bound by theory, we believe color precursors include trace amounts of impurities comprising olefinic bonds, acetals and other carbonyl compounds, peroxide-forming compounds, etc. At least some of these impurities have UV absorption that may be detected by such methods as UV spectroscopy (Test Method 4 below) or peroxide titration, etc.

The chemical PDO color quality can be measured by a UV/VIS spectrophotometer as described in Test Method 4 below.

Chemical PDO contains impurities that are either color compounds or are color precursors that form color compounds upon further processing, for example, during thermal processing in subsequent polymerization or distillation steps. These compounds give color to the chemical PDO and the polymers and polymeric objects made from chemical PDO. Chemical polymers made from chemical PDO include polyethers, polyesters, and polyether esters.

Hydrogenation has been found an effective, economical way to convert these impurities to compounds that are colorless, and which no longer have the potential to form color during subsequent processing.

Hydrogenation is achieved by contacting the chemical PDO with hydrogen in the presence of a hydrogenation catalyst. The catalyst is comprised of at least one element of Group VIII of the periodic table. Preferably, the catalyst is at least one of Ni, Co, Ru, Rh, Pd, Ir and Pt, with or without various promoters. Various mixed metal oxides such mixed copper, chromium, and zinc oxides are also effective catalysts for color removal. Hydrogenation catalysts are well known in the art and are extensively covered in "*Handbook of Heterogeneous Catalytic Hydrogenation for Organic Synthesis*" by Shigeo Nishimuru, John Wiley (2001).

The catalyst may be a porous metal structure or supported on a substrate. The catalyst support could be from any support material known in the art, such as at least one of carbon, alumina, silica, titania, silica-alumina, silica-titania, titania-alumina, clays, aluminosilicates, water insoluble salts of calcium, barium, barium sulfate, calcium carbonate, strontium carbonate, and compounds and combinations thereof. The catalyst may have various shapes or sizes, ranging from a fine powder to granules, tablets, pellets, extrudates, or other structured supports. An example of the preferred catalyst is nickel, which may be in the form of a RANEY catalyst or extrudates supported on silica/alumina.

The metal catalyst comprises at least one of RANEY nickel and RANEY cobalt catalysts which is optionally modified with at least one of iron, molybdenum, chromium, palladium, zinc or other modifying elements, or catalysts made as dispersions of these elements, or supported catalysts from the group consisting of palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina, ruthenium on silica, mixed copper and zinc oxides, and mixed copper and chromium oxides. An example of the preferred catalyst is nickel, which may be in the form of a RANEY catalyst or extrudates supported on silica/alumina.

Hydrogenation may be carried out in various gas/liquid/solid-contacting reactors known in the art. These reactors may operate in batch, semi-batch, and flow mode, using suspended or fixed bed catalysts. An industrially advantageous reactor uses a packed bed of catalyst wherein the liquid and gas flow co-currently or counter-currently, in an up-flow or down-flow (trickle-bed) mode of operation.

The variability of the UV spectra of the crude chemical PDO solution depends on the process that generated the crude PDO and also on the effectiveness of the purification steps. The extent of color reduction by hydrogenation depends on the initial color level of the crude PDO solution. For a given color level in the crude PDO solution, the desired color reduction can be achieved by selecting suitable operating conditions for hydrogenation Hydrogenation temperature affects the conversion of color or color-precursor compounds. Temperatures in the range of about 25°–250° C. can reduce color. Color reduction is faster at higher temperatures. A proper combination of contact time and temperature can achieve a desired color improvement at temperatures as low as about 25° C. While effective color reduction can be achieved in the range of about 25°–250° C., the preferred temperature ranges for PDO is about 80°–130° C., with a more preferred range of about 100°–120° C. LHSV values (LHSV=Liquid Hourly Space Velocity, units reciprocal hours, $h^{-1}$) in flow reactors are dependent on the temperature used, and should be maximized. A preferred LHSV is greater than about 0.01 $h^{-1}$. A more preferred LHSV is greater than about 1.0 $h^{-1}$, and a most preferred LHSV is greater than about 10 $h^{-1}$.

Hydrogen consumption is generally very low and depends on the level of impurities present in the crude PDO. Generally, hydrogen consumption is within the range of hydrogen solubility in the crude liquid. With the proper selection of temperature and contact time, adequate conversion can be achieved at slightly above atmospheric pressures. Above this level, an additional increase in pressure has minimal effect on the extent of color removal. Color reductions can be achieved at pressures from about ambient to 1000 psig (7000 kPa), with 200–600 psig (1480–4240 kPa) being the preferred range of pressure. A more preferred range is 300–500 psig (2170–3550 kPa). Psig denotes "pounds per square inch gauge".

The ratio of hydrogen to chemical PDO feed rate does not have a significant effect on the conversion above the stoichiometric required level of hydrogen. Effective color reductions can be achieved at 0.05–100 standard $cm^3$ of hydrogen per gram of crude PDO. The preferred range is 0.5–2 standard $cm^3$ of hydrogen and a more preferred range is 0.5–1 standard $cm^3$ of hydrogen per gram of crude PDO.

As noted above, according to one aspect of the present invention, the color of the 1,3-propanediol, after hydrogenation, is lower than the initial color of the chemical PDO. Preferably, the color, after hydrogenation, is less than about 10 APHA. More preferably, the color of the chemical PDO, after hydrogenation, is less than about 5 APHA, measured according to Test Method 1, below.

The level of color precursors in chemical PDO as measured by UV spectra is also lower after hydrogenation. Preferably, the UV absorption at 270 nm after hydrogenation is less than about 0.02 and more preferably is less than about 0.002, measured according to Test Method 4, below. In accordance with another aspect in accordance with the present invention, UV absorption of the chemical 1,3-propanediol, after hydrogenation, is reduced by at least about 50%. More preferably, the UV absorption is reduced by at least about 60%, most preferably, by at least about 70%.

In accordance with another aspect, the color of the 1,3-propanediol, after hydrogenation, has a color value less than about 15 APHA when treated with 1 wt % sulfuric acid at 170 degrees C. for 10 minutes.

According to another aspect, the hydrogenated 1,3-propenediol made in accordance with the present invention is contacted with suitable catalyst to make polyether diol or polyester diol. Suitable catalysts for this purpose are known. Preferably, the polymer so produced, has a APHA color of less than about 50, preferably, less than 30, and a molecular weight of about 250–5000, preferably about 500–4000, more preferably, about 1000–3000.

According to a further aspect in accordance with the present invention, a composition comprises (i) chemical 1,3-propanediol having color and (ii) hydrogenation catalyst (as already described herein), wherein the chemical 1,3-propanediol has a APHA color of less than about 10. Preferably, the APHA color is less than about 5 APHA.

The amount of catalyst is, preferably, the minimum amount sufficient to effect the hydrogenation, which is considered to be well within the skill of the art. As is well known to those skilled in the art, the amount of catalyst is affected by the activity of the catalyst and the presence in the composition of chemicals that reduce the activity of, or poison, the catalyst. The amount of catalyst could be as low as about 0.05% of the composition, or 0.01%, or 0.005% or even 0.001% thereof. Preferably, the hydrogenation catalyst is present in an amount not exceeding about 20% of the composition. More preferably, the hydrogenation catalyst is present in an amount not exceeding about 5% of the composition and most preferable, the hydrogenation catalyst is present in an amount not exceeding about 2% of the composition.

Materials, Equipment, and Test Methods

The chemical 1,3-propanediol is either from E.I. du Pont de Nemours and Company (Wilmington Del.), Aldrich (Milwaukee Wis.), or from other commercial sources.

Test Method 1. Color Measurement.

A Hunterlab Color Quest Spectrocolorimeter (Reston, Va.) was used to measure the PDO and polymer color. Color numbers are measured as APHA values (Platinum-Cobalt System) according to ASTM D-1209. The "b*" color of PDO is calculated from the UV/VIS spectra and computed by the instrument. Color is commonly expressed in terms of Hunter numbers which correspond to the lightness or darkness ("L") of a sample, the color value ("a*") on a red-green scale, and the color value ("b*") on a yellow-blue scale. In the context of this invention, the "b*" color value is preferably near 0.

Test Method 2. Molecular Weight Determination.

The polymer molecular weights are calculated from their hydroxyl numbers obtained by titration (Test Method 3).

Test Method 3. Hydroxyl Number.

The hydroxyl number was determined according to ASTM E222

Test Method 4. UV Absorption

The chemical PDO color quality was measured by a UV/VIS spectrophotometer. Specifically, the broad UV absorption peak at around 270–280 nm correlates strongly with the presence of color precursors in the PDO and color in the polymers made therefrom. All the UV analyses were measured using a HP 8453 UV/VIS (Hewlett-Packard, Palo Alto, Calif.) spectrophotometer after diluting the chemical PDO to a 20% concentration by volume with water. The results are reported at this 20% dilution. UV absorption at about 193 and 230 nm have less correlation with color precursors.

EXAMPLES

It should be understood that the following examples are given by way of illustration only.

General Methods:

The material and methods suitable for hydrogenation are well known in the art. In the Examples that follow, shaker-tube and up-flow fixed bed tubular reactors were used that operated in batch or flow modes using fine powder, granular, and extrudate catalysts.

Example 1

A chemical PDO was hydrogenated in an up-flow, packed catalytic reactor with an extruded catalyst (Sud-Chemie C-28-CDS) containing nominally 60% Ni on alumina/silica. About 20 g of catalyst was packed in a tubular reactor of 17.3 mm internal diameter and 129 mm length between two layers of inert glass beads. The catalyst was activated by flowing 0.44 g/min of chemical PDO and 10 standard cm$^3$ per minute of hydrogen at 400 psig (2860 kPA). The catalyst activation is carried out for 1 h at 80° C., 1 h at 100° C., and 22 h at 120° C. The actual run was carried out at a liquid hourly space velocity of 0.88 h$^{-1}$ at 100° C. and 400 psig (2860 kPa) with 5 standard cm$^3$ per minute of hydrogen flow. Hydrogenation reduced the UV-absorption at 190–270 nm (Test Method 4) as shown in Table 1. The hydrogenated chemical PDO was distilled under 15 mm Hg absolute pressure (2 kPa) and the middle 60% of distillate was taken as a purified sample. This sample showed a UV absorption peak at 270 nm of 0.01, lower than the corresponding peak of the chemical PDO before and after hydrogenation.

TABLE 1

| | UV absorption at: | | |
|---|---|---|---|
| | 193 nm | 230 nm | 270 nm |
| Chemical PDO before Hydrogenation | 2.3 | 0.17 | 0.05 |

TABLE 1-continued

| | UV absorption at: | | |
|---|---|---|---|
| | 193 nm | 230 nm | 270 nm |
| Chemical PDO after Hydrogenation | 2.1 | 0.04 | 0.02 |
| Chemical PDO after Hydrogenation and Distillation | 2.2 | 0.04 | 0.01 |

Example 2

A second chemical PDO was hydrogenated in an up-flow, packed catalytic reactor with an extruded catalyst (Sud-Chemie C-28-CDS) containing 60% Ni on alumina/silica, under conditions identical to Example 1 above. Hydrogenation reduced the UV absorption at 193–270 nm (Test Method 4) as shown in Table 2.

TABLE 2

| | UV absorption at: | | |
|---|---|---|---|
| | 193 nm | 230 nm | 270 nm |
| Chemical PDO before Hydrogenation | 2.20 | 0.08 | 0.03 |
| Chemical PDO after Hydrogenation | 2.08 | 0.02 | 0.01 |

Example 3

A third chemical PDO was hydrogenated in an up-flow, packed catalytic reactor with a RANEY 2486 Ni catalyst. In this case, 20.74 g catalyst was packed in a tubular reactor of 17.3 mm diameter to a length of 43 mm. The catalyst was activated by flowing 0.67 g/min chemical PDO and 15 standard cm$^3$ hydrogen at 400 psig (2860 kPA) and 80° C. for 24 h. The hydrogenation effect was then measured at a liquid hourly space velocity of 4 h$^{-1}$ and H2 flow rate of 15 standard cm$^3$ at 400 psig (2860 kPa). Hydrogenation reduced the UV absorption at 270 nm (Test Method 4) as shown in Table 3.

TABLE 3

| | UV absorption at: | | |
|---|---|---|---|
| | 193 nm | 230 nm | 270 nm |
| Chemical PDO before Hydrogenation | 2.18 | 0.112 | 0.023 |
| Chemical PDO after Hydrogenation at 80° C. | 2.14 | 0.080 | 0.021 |
| Chemical PDO after Hydrogenation at 100° C. | 2.06 | 0.006 | 0.001 |
| Chemical PDO after Hydrogenation 120° C. | 2.06 | 0.020 | 0.001 |

Example 4

A sample of the chemical PDO used in Example 1 and the hydrogenated and distilled chemical PDO sample from Example 1 were used to make polytrimethylene ether glycol (PO3G) from an acid catalyzed polycondensation process. The polymerization reaction was conducted in 250 mL glass reactor for 10 h at 170° C. using 1 wt % of sulfuric acid while bubbling nitrogen gas at a fixed flow rate of 0.1 L/min.

and continuously removing the water byproduct of the reaction. The molecular weight and the color of the polymers were calculated or measured from end group analysis by Test Methods 2 and 1, respectively, and shown in Table 4.

TABLE 4

Effect of hydrogenated PDO on PO3G color

| Example 4: | PO3G MW | PO3G Color, APHA |
|---|---|---|
| Chemical PDO before hydrogenation (Control) | 860 | 44 |
| Chemical PDO after hydrogenation | 790 | 18 |

The data in Table 4 clearly indicate the significant improvement in the polymer color prepared from the hydrogenated chemical PDO as opposed to chemical PDO that has not been hydrogenated. Molecular weights of the PO3G prepared are effectively identical.

Example 5

A sample of chemical PDO as used in Example 1 and the distilled and purified hydrogenated PDO sample from Example 1 were used to make polytrimethylene terephthalate (3GT) in a polycondensation process as described in "Comparative Example 1 Preparation of poly(trimethylene terephthalate) from dimethyl terephthalate (DMT) and 1,3-propanediol without mono-sodium terephthalate" in U.S. Pat. No. 6,245,844. The colors of the polymers were measured. The values are shown in Table 5.

TABLE 5

| Example 5 | 3GT Color, b* |
|---|---|
| Chemical PDO before hydrogenation (Control) | 0.058 |
| Chemical PDO after hydrogenation and distillation | −0.134 |

What is claimed is:

1. A process comprising:
   a. providing chemical 1,3-propanediol containing impurities;
   b. purifying the chemical 1,3-propanediol by hydrogenation of the impurities by contacting the chemical 1,3-propanediol with hydrogen in the presence of a hydrogenation catalyst to form a purified chemical 1,3-propanediol; and
   c. preparing polytrimethylene ether glycol, polyester, polyurethane or polyether ester from the purified chemical 1,3-propanediol.

2. The process of claim 1 wherein the impurities comprise color precursor impurities resulting from the chemical manufacture of 1,3-propanediol.

3. The process of claim 1, wherein step (c) is preparing polytrimethylene ether glycol, and is carried out by contacting the purified chemical 1,3-propanediol with a polycondensation catalyst.

4. The process of claim 1, further comprising preparing the chemical 1,3-propanediol by a hydroformylation route from ethylene oxide.

5. The process of claim 1, further comprising preparing the chemical 1,3-propanediol by catalytic solution phase hydration of acrolein followed by reduction.

6. The process of claim 1, wherein (a) before purifying the chemical 1,3-propanediol has an initial color and (b) after purifying the chemical 1,3-propanediol has a color lower than the initial color.

7. The process of claim 3, further comprising, after step b, adding a suitable antioxidant.

8. The process of claim 1, wherein the hydrogenation catalyst comprises at least one element of Group VIII of the Periodic Table or a metal oxide.

9. The process of claim 8 wherein the hydrogenation catalyst is supported on a support comprised of at least one of carbon, alumina, silica, titania, silica-alumina, silica-titania, titania-alumina, clays, aluminosilicates, water insoluble salts of calcium, barium, barium sulfate, calcium carbonate, strontium carbonate, and compounds and combinations thereof.

10. The process of claim 8, wherein the hydrogenation catalyst is at least one of Ni, Co, Ru, Rh, Pd, Ir and Pt, with or without various promoters.

11. The process of claim 1, wherein the hydrogenation catalyst is the metal oxide and the metal oxide is a mixed metal oxide selected from the group consisting of mixed copper, chromium, and zinc oxides.

12. The process of claim 1, wherein the hydrogenation catalyst comprises at least one of RANEY nickel and RANEY cobalt catalyst which is optionally modified with at least one of iron, molybdenum, chromium, palladium, zinc or other modifying elements, or catalysts made as dispersions of these elements, or supported catalysts from the group consisting of palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina, ruthenium on silica, mixed copper oxide, zinc oxides, and chromium oxides.

13. The process of claim 1, wherein the purifying is conducted at a temperature of about 25° C. to about 250° C. and a pressure of about ambient to about 1000 psig; the amount of hydrogen contacted with the 1,3-propanediol is about 0.05 to about 100 standard $cm^3$ per gram of 1,3-propanediol.

14. The process of claim 13, wherein the purifying is carried out using about 0.01% to 20% of the hydrogenation catalyst, by weight of the chemical 1,3-propanediol.

15. The process of claim 1, wherein the purifying is conducted at a temperature of about 80° C. to about 130° C. and a pressure of 200 to 600 psig, and the amount of hydrogen contacted with the 1,3-propanediol is 0.5–2 standard $cm^3$ per gram of 1,3-propanediol.

16. The process of claim 15, wherein the purifying is carried out using about 0.005% to 5% of the hydrogenation catalyst, by weight of the chemical 1,3-propanediol.

17. The process of claim 15, wherein the purifying is carried out using about 0.05% to 2% of the hydrogenation catalyst, by weight of the chemical 1,3-propanediol.

18. The process of claim 16, wherein the purifying is conducted at a temperature of about 100° C. to about 120° C.

19. The process of claim 1, wherein the hydrogenation is carried out in a flow reactor and the Liquid Hourly Space Velocity is at greater than about 0.01 $h^{-1}$.

20. The process of claim 19, wherein the Liquid Hourly Space Velocity is greater than about 10 $h^{-1}$.

21. The process of claim 3, wherein the polycondensation catalyst is selected from the group consisting of sulfuric acid, fluorosulfonic acid, phosphorus acid, p-toluenesulfonic acid, benzenesulfonic acid, phosphotungstic acid, phosphomolybdic acid, trifluoromethanesulfonic acid, 1,1,2,2-tetrafluoroethanesulfonic acid, 1,1,1,2,3,3-hexafluoropropanesulfonic acid, bismuth triflate, yttrium triflate, scandium triflate and zirconium triflate.

22. The process of claim 2, wherein the UV absorption of the chemical 1,3-propanediol is reduced by at least about 50% by the purification, and the UV absorption of the purified chemical 1,3-propanediol at 270 nm is less than about 0.02.

23. The process of claim 14 wherein the impurities comprise color precursor impurities resulting from the chemical manufacture of 1,3-propanediol, the hydrogenation catalyst comprises at least one element of Group VIII of the Periodic Table or a metal oxide, the puritying is carried out using about 0.05% to 2% of the hydrogenation catalyst, by weight of the chemical 1,3-propanediol, the step (c) is the preparing polytrimethylene ether glycol, and the preparing polytrimethylene ether glycol is carried out by contacting the purified chemical 1,3-propanediol with a polycondensation catalyst.

* * * * *